United States Patent
Xu et al.

(10) Patent No.: US 10,513,527 B2
(45) Date of Patent: Dec. 24, 2019

(54) PROCESS FOR PREPARING DARUNAVIR AMORPHOUS

(71) Applicant: Zhejiang Jiuzhou Pharmaceutical Co., Ltd., Taizhou (CN)

(72) Inventors: Jiankang Xu, Taizhou (CN); Hao Wu, Taizhou (CN); Meiqi Ye, Taizhou (CN); Kai Ye, Taizhou (CN); Linbing Zhu, Taizhou (CN)

( * ) Notice: Subject to any disclaimer, the term of this patent is extended or adjusted under 35 U.S.C. 154(b) by 0 days.

(21) Appl. No.: 15/780,642

(22) PCT Filed: Jan. 8, 2016

(86) PCT No.: PCT/CN2016/070494
§ 371 (c)(1),
(2) Date: Jun. 1, 2018

(87) PCT Pub. No.: WO2017/096690
PCT Pub. Date: Jun. 15, 2017

(65) Prior Publication Data
US 2018/0362539 A1  Dec. 20, 2018

(30) Foreign Application Priority Data

Dec. 8, 2015 (CN) .......................... 2015 1 0894282

(51) Int. Cl.
*C07D 493/00* (2006.01)
*C07D 493/04* (2006.01)

(52) U.S. Cl.
CPC .................................. *C07D 493/04* (2013.01)

(58) Field of Classification Search
CPC .................................................. C07D 493/04
(Continued)

(56) References Cited

U.S. PATENT DOCUMENTS

2012/0035142 A1  2/2012  Marom

FOREIGN PATENT DOCUMENTS

CN   103509031 A    1/2014
WO   WO2013/114382  *  8/2013

* cited by examiner

*Primary Examiner* — Taylor V Oh

(57) ABSTRACT

The present invention relates to medical chemistry technique field, particularly relates to a preparation method for amorphous darunavir crystal,

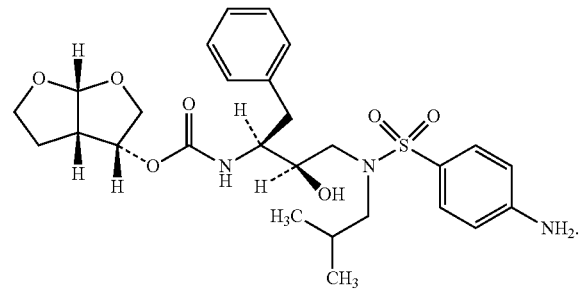

The present invention provides a preparation method for preparing amorphous form of darunavir using an anti-solvent method. It can be a different method compared to the evaporation and concentration process disclosed in WO2011048604. Although the same with WO2013114382, anti-solvent are used, the target crystal form are truly different. The crystal form of WO2013114382 is solvent-free darunavir crystal, while an amorphous form of darunavir in the present application.

9 Claims, 1 Drawing Sheet

(58) Field of Classification Search
USPC .......................................................... 549/464
See application file for complete search history.

PROCESS FOR PREPARING DARUNAVIR AMORPHOUS

TECHNICAL FIELD

The present invention relates to medical chemistry technical field, particular relates to process for the preparation of amorphous Darunavir.

BACKGROUND

Among development of drug polymorphs, two kinds of research way are the preferable way to be commonly used, one named multiple crystal selecting, while the other named being salt selecting. Multiple crystal selecting is that using some certain method to make the compound to form polymorphs in multiple different solvents. The common used method in multiple crystal selecting are: suspended balance method, solvent heating cooling method, saturated solution naturally evaporated method, anti-solvent adding method. Being salt selecting is that drugs reacted with different anti-ions (acid or base) to form a salt, in the reaction, the force between drugs with the acid or salt is primarily ion bond forms to produce reaction and effect.

darunavir, with chemical name [(1R,5S,6R)-2,8-bioxybiocyclo[3.3.0]-decane-6-yl]-N-[(2S,3R)-4-[(4-amino phenyl)sulfonyl-(2-methyl propyl)amino]-3-hydroxyl-1-phenyl-butane-2-yl] carbamic acid ester,

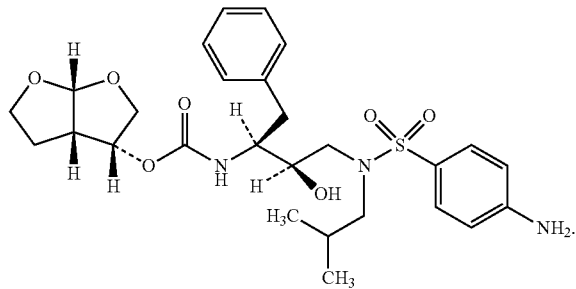 [SMILES: CC(C)CN(C[C@@H](O)[C@H](Cc1ccccc1)NC(=O)O[C@H]1CO[C@H]2OCC[C@H]21)S(=O)(=O)c1ccc(N)cc1]

Darunavir is an inhibitor of protease, marketed with its ethanolate form in U.S.A in July 2006, the market name is Prezista. Darunavir exists in polymorphs, many manufactures have done much research work in it including its drug polymorphs and amorphous. Also, patent applications are filed about this product.

For example in WO2011048604 (applicant: MATRIX LABORATORIES LIMITED, publication date: Apr. 28, 2011), amorphous darunavir is obtained through a method of evaporation and concentration process. The detailed can be described as the following procedure, in a solvent such as ethyl acetate, darunavir was dissolved in, removing the solvent by concentration to form semi-solid, the hydro carbon solvent such as heptane was added, the amorphous darunavir crystal can be obtained after isolating. Usually, some drawbacks are existed when evaporation and concentration method are used: first is material easily to be bulked, special vacuum equipment need to be used in commercialized industry production, it can lead to the decrease of capacity; second is after the commercialized industry production, with the increase of solvent amount, it can lead to long time distillation process and also production cycle period lengthened accordingly. What's more, large amounts of waste gases are produced during evaporation and concentration process.

For example, in WO2013114382 (Applicant: MYLAN LABORATORIES LTD, publication date: Aug. 8, 2013), it took the following synthesis steps, in the solvent of acetate ester, darunavir was dissolved in, then adding heptane in to it as the anti-solvent, the anhydrate darunavir crystal was obtained. Although the application also uses the anti-solvent method, and no evaporation and concentration method defects existed, the solvent-free darunavir crystal was produced, not an amorphous form disclosed in the present application.

The present invention provides a preparation method for preparing amorphous form of darunavir using an anti-solvent method. It can be a different method compared to the evaporation and concentration process disclosed in WO2011048604. Although the same with WO2013114382, anti-solvent are used, the target crystal form are truly different. The crystal form of WO2013114382 is solvent-free darunavir crystal, while an amorphous form of darunavir in the present application.

SUMMARY OF INVENTION

The present invention provides a preparation method for preparing an amorphous form of darunavir using anti-solvent. The preparation method has the advantages of simple process, no special equipment needed, short producing cycle, large production etc. And the preparation method is suitable for commercialized industry production.

To realize the objection of the present invention, the following technical proposal has been taken in the present invention:

The preparation method provided by the present invention, comprising the following steps:

a. Darunavir was added into the soluble solvent, b. after dissolved, take them into the anti-solvent, c. isolated to obtain amorphous darunavir crystal.

wherein, the said soluble solvent is selected from one of ester solvent or ketones solvent or mixture of them; to be preferable, the said soluble solvent is selected from ester solvent. The said ester solvent can be ethyl formate, acetate ester or isopropyl acetate etc; the said ketones can be acetone, methyl ethyl ketone, MIBK or methyl n-butyl ketone.

The said anti-solvent can be the solvent which contains hydro carbon compound or ethers solvent; to be preferable, the said anti-solvent is the solvent which contains hydro carbon compound. The said solvent which contains hydro carbon compound can be C5~C12 alkanes, arenes or mixture of them, wherein, the C5~C12 alkanes can be selected from one of heptane, hexane, cyclohexane, methyl cyclohexane or mixture of them; The said arenes can be toluene or xylol; The said ethers can be methyl Tertiary Butyl Ether or isopropyl ether.

Further, the present invention provides a preparation method to prepare an amorphous darunavir crystal, comprising the following steps:

a. Adding darunavir into the soluble solvent, b. after dissolved, take it into anti-solvent at a certain temperature, c. isolated to obtain amorphous darunavir crystal.

Wherein, the said certain temperature is −30° C.~30° C., preferably, the said certain temperature is −10° C.~10° C.

To be a further aspect, the preparation method disclosed in the present invention, comprises the following procedure:

a. Adding darunavir into the soluble solvent, b. after dissolved to form clear solution, take it into anti-solvent at a certain temperature, c. isolated to obtain amorphous darunavir crystal.

Wherein, to form clear solution, the operation such as stirring the solution or heating the temperature can be used. The temperature can be heated from room temperature to the boiling point of the solvent.

In the present invention technical proposal, the quality ratio of darunavir soluble solvent with anti-solvent can be 1:1~50, preferably, 1:1~20.

The more detailed aspect of the present invention can be:
a. Adding 10 g darunavir into the soluble solvent such as 50 g isopropyl acetate, b. dissolved when clear solution formed, take it into anti-solvent at a certain temperature of −10° C.~10° C., c. isolated to obtain amorphous darunavir crystal.

X ray powder diffraction is taken to measure amorphous form of darunavir in the present invention.

The present invention provides a method to prepare an amorphous darunavir crystal using anti-solvent method, namely, taking darunavir solution into the cooled anti-solvent to be crystallization, then separate out amorphous darunavir crystal. The preparation method is simple, no special equipment being used, short production cycle, large capacity, suitable for industry production. The obtained product according to the preparation method disclosed in the present invention has the advantage of good solubility.

DRAWINGS

SPECIFIC EMBODIMENT

To better understand the contents of the present invention, further description incorporated with the specific examples are described. It should be noted that the specific embodiment is not to form a limit to the contents of the present invention.

The examining condition of the present invention

Instrument: Bruker D2 Phaser X-ray powder diffraction instrument

X-ray powder diffraction target material: Cu Kα (1.54184 A);

Tube pressure: 30 kV;
Tube flow: 10 mA;
2 θ scanning scope: 2°-40°;
Scanning rate (chasse) 0.2 s/step;
Step size: 0.02°.

Example 1

Figure 1:
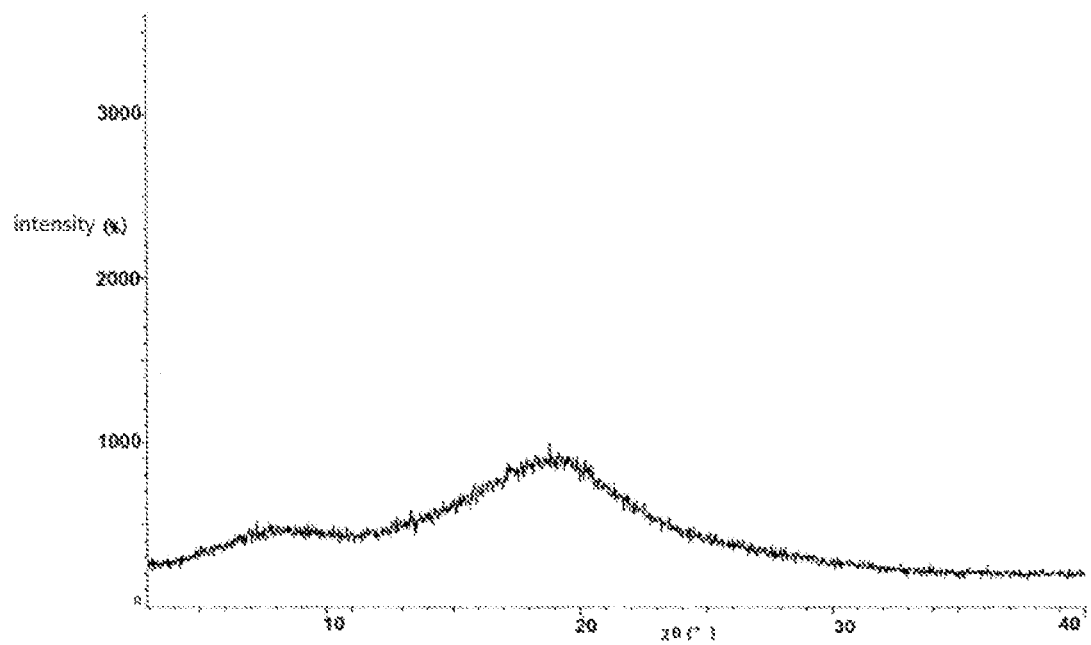
FIG. 1 illustrates the XRPD spectrum of amorphous darunavir crystal prepared from the Example 1.

Into the 250 ml quadrangle bottle, 50 g isopropyl acetate and 10 g darunavir were added, stirred, the mixture was heated to 50-60° C.; after the solution was clear, take the solution into n-heptane at a temperature of 0~5° C., after the adding, keep the temperature for 1-3 hours. Suction filtrated, the mixture was eluted by n-heptane. The wet product was dried on a vacuum oven at the temperature of 60° C. The amorphous darunavir crystal was obtained with the yield of 9.3 g (93.0%), the purity is 100.0%. The XPRD spectrum is shown by FIG. 1.

Example 2

Figure 2:
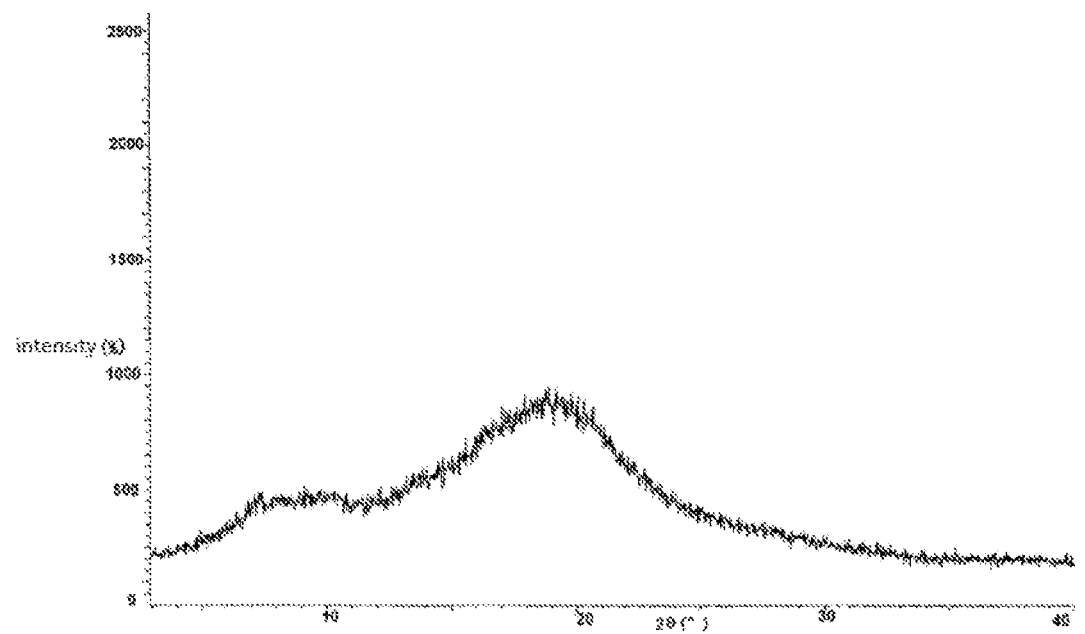
FIG. 2 illustrates the XRPD spectrum of amorphous darunavir crystal prepared from the Example 2.

Into the 250 ml quadrangle bottle, 4 g acetone and 1 g darunavir were added, stirred, the mixture was heated to 50-60° C.; after the solution was clear, take the solution into n-heptane at a temperature of 0~5° C., after the adding, keep the temperature for 1-3 hours. Suction filtrated, the mixture was eluted by n-heptane. The wet product was dried on a vacuum oven at the temperature of 60° C. The amorphous darunavir crystal was obtained with the yield of 0.95 g (95.0%), the purity is 99.9%. The XPRD spectrum is shown by FIG. 2.

Example 3

Into the 250 ml quadrangle bottle, 50 g isopropyl acetate and 10 g darunavir were added, stirred, the mixture was heated to 50-60° C.; after the solution was clear, take the solution into n-heptane at a temperature of −10~0° C., Suction filtrated, the mixture was eluted by n-heptane. The wet product was dried on a vacuum oven at the temperature of 60° C. The amorphous darunavir crystal was obtained with the yield of 9.3 g (93.0%), the purity is 100.0%.

Example 4

Into the 250 ml quadrangle bottle, 50 g isopropyl acetate and 10 g darunavir were added, stirred, the mixture was heated to 50-60° C.; after the solution was clear, take the solution into n-heptane at a temperature of 5~10° C., Suction filtrated, the mixture was eluted by n-heptane. The wet product was dried on a vacuum oven at the temperature of 60° C. The amorphous darunavir crystal was obtained with the yield of 9.3 g (93.0%), the purity is 100.0%.

The invention claimed is:

1. A preparation method of an amorphous darunavir crystal, wherein, comprising the following steps:
   a. Adding darunavir into the soluble solvent, b. after dissolved, take it into anti-solvent, c. isolated to obtain amorphous darunavir crystal;
   the anti-solvent is C5~C12 alkanes.

2. The preparation method of an amorphous darunavir crystal according to claim 1, wherein, comprising the following steps:
   a. Adding darunavir into the soluble solvent, b. after dissolved, take it into anti-solvent at a certain temperature, c. isolated to obtain amorphous darunavir crystal;
   the anti-solvent is C5~C12 alkanes.

3. The preparation method of an amorphous darunavir crystal according to claim 1, wherein, comprising the following steps:
   a. Adding darunavir into the soluble solvent, b. after dissolved to be a clear solution, take it into anti-solvent at a certain temperature, c. isolated to obtain amorphous darunavir crystal; the anti-solvent is C5~C12 alkanes.

4. The preparation method of an amorphous darunavir crystal according to claim 1, wherein, comprising the following steps:
   a. Adding darunavir into the soluble solvent, b. after dissolved to be a clear solution at the temperature of room temperature to the boiling of the solvent, take it into anti-solvent at a certain temperature, c. isolated to obtain amorphous darunavir crystal; the anti-solvent is C5~C12 alkanes.

5. The preparation method according to claim 1, 2, 3 or 4, wherein, the said soluble solvent is selected from any one of esters or ketones or mixture of them; the said anti-solvent is hydrocarbon solvent or ethers.

6. The preparation method according to claim 5, wherein, said ester solvent is ethyl formate, acetate ester or isopropyl acetate; the said ketones is acetone, methyl ethyl ketone, MIBK or methyl n-butyl ketone.

7. The preparation method according to claim 1, 2, 3 or 4, wherein, the C5~C12 alkanes is selected from one of heptane, hexane, cyclohexane, methyl cyclohexane or mixture of them.

8. The preparation method according to claim 2, 3 or 4, wherein, the temperature is −30° C.~30° C.

9. The preparation method according to claim 1, 2, 3 or 4, wherein, the quality ratio of darunavir soluble solvent with anti-solvent is 1:1~50.

* * * * *